(12) United States Patent
Trombetta et al.

(10) Patent No.: US 10,379,025 B2
(45) Date of Patent: Aug. 13, 2019

(54) APPARATUS FOR TESTING OF WATER PERMEABILITY OF SAMPLES OF BUILDING FACADES

(71) Applicant: UNIVERSITÀ DEGLI STUDI "MEDITERRANEA" DI REGGIO CALABRIA, Reggio Calabria (IT)

(72) Inventors: Corrado Trombetta, Reggio Calabria (IT); Martino Milardi, Reggio Calabria (IT); Massimo Rossetti, Reggio Calabria (IT)

(73) Assignee: UNIVERSITÀ DEGLI STUDI "MEDITERRANEA" DI REGGIO CALABRIA, Reggio Calabria (IT)

(*) Notice: Subject to any disclaimer, the term of this patent is extended or adjusted under 35 U.S.C. 154(b) by 197 days.

(21) Appl. No.: 15/555,984

(22) PCT Filed: Jan. 4, 2016

(86) PCT No.: PCT/IB2016/050011
§ 371 (c)(1),
(2) Date: Sep. 6, 2017

(87) PCT Pub. No.: WO2016/108213
PCT Pub. Date: Jul. 7, 2016

(65) Prior Publication Data
US 2018/0052092 A1     Feb. 22, 2018

(30) Foreign Application Priority Data
Dec. 31, 2014  (IT) .............................. CS2014A0035

(51) Int. Cl.
*B05B 1/14* (2006.01)
*B05B 13/02* (2006.01)
(Continued)

(52) U.S. Cl.
CPC ......... *G01N 15/082* (2013.01); *G01N 33/383* (2013.01); *B05B 1/14* (2013.01);
(Continued)

(58) Field of Classification Search
CPC ....... B05B 15/70; B05B 13/0278; B05B 1/14; B05B 13/0285; G01N 15/08
See application file for complete search history.

(56) References Cited

U.S. PATENT DOCUMENTS 1,187,349 A * 6/1916 Libby ................... B05B 15/656
                                                       239/281
4,872,417 A * 10/1989 Kuwabara ............... B05B 12/06
                                                       118/411
(Continued)

*Primary Examiner* — David A Rogers
(74) *Attorney, Agent, or Firm* — Mark M. Friedman

(57) ABSTRACT

Apparatus for testing of the water permeability of samples of building facades comprising a frame (3) on one side of which a sample of the facade to be tested (2) is fixed, and a grid (5) on which nozzles (1) which spray water on the sample of the facade to be tested (2) are arranged, characterized in that said apparatus is equipped with a movement system (4) of the grid (5) from a working position positioned in front of the facade sample to be tested (2) to a rest position positioned behind the frame (3) on the opposite side to that on which is located the sample (2) and that the grid (5) on which nozzles (1) are set up slides on elements of the frame placed at a predetermined distance from the sample to be tested (2).

10 Claims, 2 Drawing Sheets

(51) Int. Cl.
*B05B 15/70* (2018.01)
*G01N 15/08* (2006.01)
*G01N 33/38* (2006.01)

(52) U.S. Cl.
CPC ....... *B05B 13/0278* (2013.01); *B05B 13/0285* (2013.01); *B05B 15/70* (2018.02)

(56) References Cited

U.S. PATENT DOCUMENTS

| | | | | |
|---|---|---|---|---|
| 4,936,330 A * | 6/1990 | LaHue | ...................... | B60S 3/04 134/123 |
| 5,240,503 A * | 8/1993 | Levy | ........................ | A47L 1/02 118/323 |
| 5,266,115 A * | 11/1993 | Taccon | ................ | B05B 13/0431 118/663 |
| 5,280,855 A * | 1/1994 | Rietsch, Jr. | ......... | B05B 13/0405 134/123 |
| 5,346,140 A * | 9/1994 | Campbell | ........... | B05B 13/0415 239/243 |
| 5,494,227 A * | 2/1996 | Costantini | ........... | B05B 13/0278 134/172 |
| 5,526,983 A * | 6/1996 | Petit | .................... | B05B 13/0405 134/123 |
| 5,725,003 A * | 3/1998 | Jaakkonen | ................ | B60S 3/04 134/123 |
| 6,158,678 A * | 12/2000 | Lange | .................... | A47L 11/38 239/532 |
| 6,679,275 B2 * | 1/2004 | Heinze | ..................... | B60S 3/04 134/123 |
| 7,156,323 B2 * | 1/2007 | Mikkelson | .............. | G01M 3/02 239/207 |
| 9,459,192 B2 * | 10/2016 | Hosoda | ................ | G01N 33/383 |
| 2017/0095828 A1 * | 4/2017 | Ripley | .................... | B05B 15/70 |
| 2018/0169687 A1 * | 6/2018 | Vasa | ...................... | B05D 7/00 |

* cited by examiner

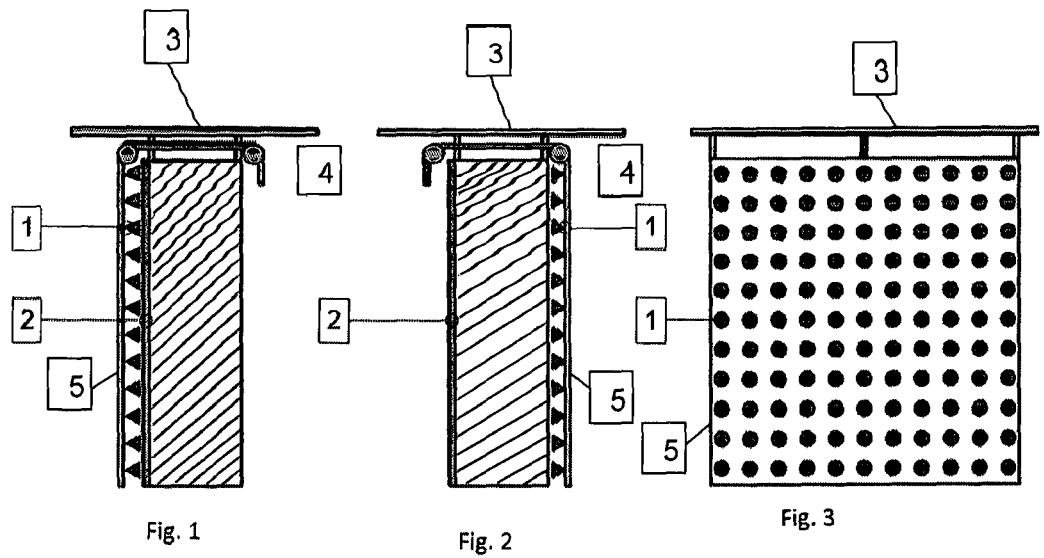
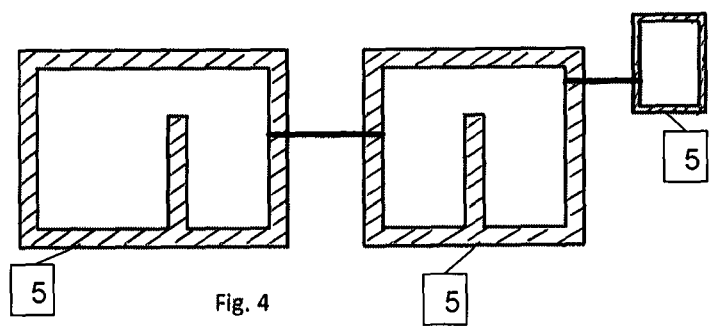

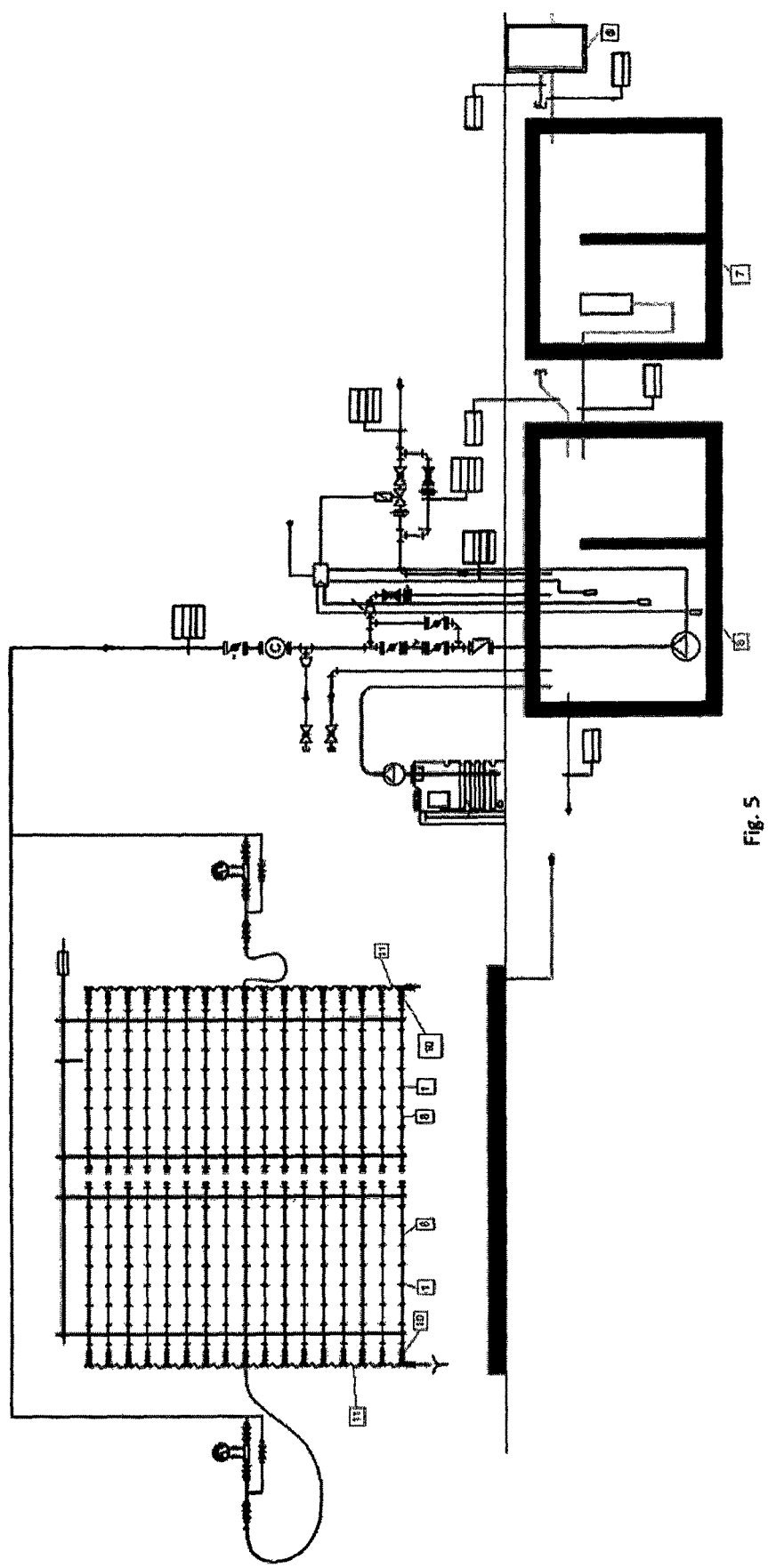

APPARATUS FOR TESTING OF WATER PERMEABILITY OF SAMPLES OF BUILDING FACADES

TECHNICAL FIELD OF THE INVENTION

The present invention relates to an apparatus for the testing of the water permeability of samples of building facades, the tests which may be performed concern mainly, but not exclusively, water and wind tightness tests.

STATE OF THE ART

The water permeability test equipment on samples of building facades used so far have basically made use of two systems:

System Built "on Site" on the Sample

This system has several disadvantages such as long positioning times—small chance of total recovery of materials long time of calibration of the fluxes and flow rates; number of tests/year strongly limited by the sequence of operations required, with the result of obtaining a limited productivity of the laboratory, the need for highly specialized workers,— the need to provide dedicated mounting devices, platforms, scaffolds.

System Assembled on Trucks

This system has the following disadvantages; Dimensions of sample is limited by the size of vertical pipes; difficulties in the handling of cargo due to center of gravity positioned in a disadvantageous way; occupation of space for equipment storage when not in use; stability problems due to the influence of the wind, or even of the wind simulator, due to the exposed surface, with the risk of overturning in the event of sudden gusts; long positioning times; high exposure of the workers to "residues" risks of the equipment, before, during and after the test; need for highly skilled workers.

A device that uses a system assembled on trucks is described in CN202770820.

DESCRIPTION OF THE INVENTION

To overcome these and other disadvantages present in the equipment currently on the market has been realized an apparatus for the testing of the water permeability of samples of building facades comprising a frame on one side of which a sample of the facade to be tested is fixed, and a grid on which nozzles which spray water on the sample of the facade to be tested are arranged, characterized in that said apparatus is equipped with a movement system of the grid from a working position positioned in front of the facade sample to be tested to a rest position positioned behind the frame on the opposite side to that on which is located the sample and that the grid on which nozzles are set up slides on elements of the frame placed at a predetermined distance from the sample to be tested.

The apparatus object of the present invention allows to rapidly position the sample on said test apparatus, to position said sample at the right distance from the nozzles which have to spray the water to flood, to carry out the calibration of the fluxes and flow rates in times shorter compared to the systems currently in use.

Another characteristic is given by the fact that the nozzles are fed from parallel tubes placed at a predetermined distance from each other.

Another characteristic is given by the fact that the tubes are fed by a distribution column placed at one end of each tube.

Another characteristic is given by the fact that the tubes are interrupted at the center and each half tube is supplied from a distribution column placed at one end of each half tube.

With the apparatus object of the present invention can be put into test samples of different sizes by partializing the water supply system or it is possible to perform tests on multiple samples mounted on the same equipment. Another characteristic is given by the fact that the tubes fed by a distribution column placed at one end of each tube or half tube are connected with a sleeve.

Another characteristic is given by the fact that said apparatus is equipped with a system of collection and recycling of water.

Another characteristic is given by the fact that the system of collection and recycling of water is composed of a collection well, of a collection tank of first rain coming from the open area on which said apparatus is positioned and a sedimentation and storage tank from which water is drawn to supply testing. The apparatus object of the present invention has the advantage of re-use both the water used in the test and the rainwater that falls in the site where the tests are made and the waste water is practically reduced to a minimum.

Other features and advantages of the present invention will become clear from the description hereinafter of an embodiment of the present invention given by way of non-limiting example in FIGS. 1, 2, 3, 4 and 5.

BRIEF DESCRIPTION OF FIGURES

FIG. 1 is a longitudinal section of the apparatus object of the present invention with the grid that brings the nozzles in the working position;

FIG. 2 is a longitudinal section of the apparatus object of the present invention with the grid that brings the nozzles in the rest position;

FIG. 3 is a front view of the grid that carries the nozzles of the apparatus object of the present invention;

FIG. 4 is a longitudinal section of the tanks of the water system of the apparatus object of the present invention;

FIG. 5 is a schematic view of the water system of the apparatus object of the present invention.

DETAILED DESCRIPTION OF AN EMBODIMENT OF THE PRESENT INVENTION

The apparatus object of the present invention, with reference to the figures, is composed of a frame 3 on one side of which is fixed a sample of the facade to test 2, and by a grid 5 on which the nozzles 1 are arranged which spray water on the facade sample to be tested 2. The apparatus is also equipped with a moving system 4 of the grid 5 from a working position located in front of the facade of the sample to be tested 2 to a rest position placed behind the frame on the opposite side to that on which the sample 2 is located. In a preferred embodiment, but not exclusive, illustrated in detail in FIGS. 1-4 and in the complex in FIG. 5, the grid 5 on which the nozzles 1 are arranged is showed, the movement system 4 of the grid 5 is constituted mainly, but not exclusively, by a chain transmission equipped with meshes with the hanger supporting pipes 8 preferably, but not exclusively in light alloy. The grid 5 on which are arranged the nozzles 1 slides on the frame elements and, therefore, is obliged by the movement system 4 to be arranged at a predetermined distance from the sample 2 to be tested.

The nozzles 1 are fed by pipes 8 arranged parallel to one another at predetermined distance to meet the standards that rules the testing of tightness and the combined action of rain and wind. The pipes 8 are preferably, but not exclusively in light alloy but may be in any suitable material.

The pipes 8 are connected on each side by means of a distribution column 11 that has many branches as tubes 8 are to be fed by means of connecting sleeves 10. In this way it is possible to use the equipment for different surfaces, depending on whether they feed the two sides or only one or if one feeds a reduced number of tubes.

The pipes 8 are fed by a water system with a pumping system that provides for the collection and recirculation of the water for carrying out the tests and its reuse for other test cycles; The water system includes a collection sump 6 eventually covered by a grid positioned immediately below the sample of the test wall, a tub of first rain collection 7 of the yard and a sedimentation and storage tank 8 from which water is drawn for feeding the tests. The apparatus object of the present invention allows to make water permeability tests on samples of facades without having to move the equipment on the wall to be tested.

The facade sample 2 may be of considerable size, also 10.00×20.00 meters, but also larger dimensions are possible, said facade sample 2 is easily installed on the frame 3, said sample is already located in this position at the distance planned to make the tests according to the standards laid down by European or international official regulations and subsequent adjustments are not required. The tests are repeatable in considerably shorter times than those that occur using the equipments currently available on the market.

Furthermore, the technical solution pertains not to the criteria with fixed test modules but it is constructed so as to be collected and housed on the same test structure.

The solution offers the possibility to carry out a greater number of tests, it can be made more flexible through a deferrable modularity, to ensure greater variability to the test conditions, to offer more opportunities to experiment on their own because of the different configuration of the nozzles for water permeability tests.

The invention provides a semi-automatic positioning solution of the nozzles on the front facade.

Briefly, the nozzles are lowered from the top down through a "gate" type system.

The grid 5 with the nozzles 1, in rest conditions, is made to slide in the rear part of the frame 3, i.e. in a position free of interference with other equipment and without increasing the space necessary for admission of the test apparatus. The invention, it should be noted, is not limited to the representations given in the figures, but may be perfected and modified by those skilled in the art without, however, exceeding the limits of patent.

The invention permits numerous advantages, and to overcome difficulties that could not otherwise have been overcome with the systems on sale at present.

The invention claimed is:

1. Apparatus for testing of the water permeability of samples of building facades comprising a frame (3) on one side of which a sample of the facade to be tested (2) is fixed, and a grid (5) on which nozzles (1) which spray water on the sample of the facade to be tested (2) are arranged, characterized in that said apparatus is equipped with a movement system (4) of the grid (5) from working position positioned in front of the facade sample to be tested (2) to a rest position positioned behind the frame (3) on the opposite side to that on which is located the sample (2) and that the grid (5) on which nozzles (1) are set up slides on elements of the frame placed at a predetermined distance from the sample to be tested (2).

2. Apparatus for testing water permeability of samples of building facades according to claim 1 characterized in that the nozzles are fed by parallel tubes placed at a predetermined distance from each other.

3. Apparatus for testing water permeability of samples of building facades according to claim 2 characterized in that the tubes are fed by a distribution column placed at one end of each tube.

4. Apparatus for testing water permeability of samples of building facades according to claim 3, characterized in that the tubes fed by a distribution column placed at one end of each tube or half tube are connected with a sleeve.

5. Apparatus for testing water permeability of samples of building facades according to claim 2 characterized in that the tubes are interrupted at the center and each half tube is supplied from a distribution column placed at one end of each half tube.

6. Apparatus for testing water permeability of samples of building facades according to claim 5, characterized in that said apparatus is equipped with a system of collection and recycling of water.

7. Apparatus for testing water permeability of samples of building facades according to claim 2 characterized in that said apparatus is equipped with a system of collection and recycling of water.

8. Apparatus for testing water permeability of samples of building facades according to claim 7 characterized in that the system of collection and recycling of water is composed of a collection well (6), of a collection tank of first rain (7) coming from the open area on which said apparatus is positioned ad a sedimentation and storage tank (8) from which water is drawn to supply testing.

9. Apparatus for testing water permeability of samples of building facades according to claim 1 characterized in that equipped with a system of collection and recycling of water.

10. Apparatus for testing water permeability of samples of building facades according to claim 9 characterized in that the system of collection and recycling of water is composed of a collection well (6), of a collection tank of first rain (7) coming from the open area on which said apparatus is positioned and a sedimentation and storage tank (8) from which water is drawn to supply testing.

* * * * *